(12) United States Patent
Inoue et al.

(10) Patent No.: US 7,783,487 B2
(45) Date of Patent: Aug. 24, 2010

(54) INFORMATION PROCESSING TERMINAL AND COMMUNICATION SYSTEM

(75) Inventors: Akiko Inoue, Saitama (JP); Yoichiro Sako, Tokyo (JP); Toshiro Terauchi, Tokyo (JP); Makoto Inoue, Kanagawa (JP); Katsuya Shirai, Kanagawa (JP); Yasushi Miyajima, Kanagawa (JP); Kenichi Makino, Kanagawa (JP); Motoyuki Takai, Tokyo (JP)

(73) Assignee: Sony Corporation, Tokyo (JP)

( * ) Notice: Subject to any disclaimer, the term of this patent is extended or adjusted under 35 U.S.C. 154(b) by 1235 days.

(21) Appl. No.: 10/567,450

(22) PCT Filed: Aug. 13, 2004

(86) PCT No.: PCT/JP2004/011706

§ 371 (c)(1),
(2), (4) Date: Feb. 7, 2006

(87) PCT Pub. No.: WO2005/016147

PCT Pub. Date: Feb. 24, 2005

(65) Prior Publication Data

US 2008/0167861 A1 Jul. 10, 2008

(30) Foreign Application Priority Data

Aug. 14, 2003 (JP) ............................... 2003-293567

(51) Int. Cl.
*G10L 13/00* (2006.01)
(52) U.S. Cl. ...................................... 704/270; 704/260
(58) Field of Classification Search .................. 704/270, 704/260; 715/706

See application file for complete search history.

(56) References Cited

U.S. PATENT DOCUMENTS

| 5,974,262 | A | * | 10/1999 | Fuller et al. | .................... | 710/18 |
| 7,360,151 | B1 | * | 4/2008 | Froloff | ........................ | 715/255 |
| 2001/0001318 | A1 | * | 5/2001 | Kamiya et al. | .............. | 700/246 |
| 2002/0198717 | A1 | * | 12/2002 | Oudeyer et al. | ............. | 704/270 |
| 2003/0182123 | A1 | * | 9/2003 | Mitsuyoshi | ................. | 704/270 |

FOREIGN PATENT DOCUMENTS

JP 2001-125900 5/2001

(Continued)

*Primary Examiner*—Daniel D Abebe
(74) *Attorney, Agent, or Firm*—Oblon, Spivak, McClelland, Maier & Neustadt, L.L.P.

(57) ABSTRACT

There is provided a mobile phone that detects bio-information on the user and makes information communications reflecting the detected bio-information. The mobile phone (1) includes sensors (18) that detect bio-information data. The bio-information data detected by the sensors (18) are sent to a sensor data analyzer (19) in which psychology corresponding to the detected bio-information data is analyzed based on bio-information data stored in a psychology memory (20) and psychology of the user. The sensor data analyzer (19) extracts characteristic signal patterns from the bio-information data detected by the sensors (18) and analyzes psychology corresponding to the extracted signal patterns. The psychology includes, for example, "pleased and delightful", "discouraged", "excited", etc. and these states of mind are stored in association with bio-information data in the psychology memory (20). When the bio-information data are detected by the sensors (18), psychology most matching the bio-information data is selectively read out of the psychology memory (20).

32 Claims, 6 Drawing Sheets

FOREIGN PATENT DOCUMENTS

| | | |
|---|---|---|
| JP | 2001-344352 | 12/2001 |
| JP | 2002-34936 | 2/2002 |
| JP | 2002-263107 | 9/2002 |
| JP | 2003-018250 | 1/2003 |
| JP | 2003-18250 | 1/2003 |
| JP | 2003-153905 | 5/2003 |
| JP | 2004-320544 | 11/2004 |
| WO | WO 01/39584 A2 | 6/2001 |

\* cited by examiner

| Category | Basic word | Characteristic word | ... |
|---|---|---|---|
| Salutation | Good morning | Good day | ... |
| | Good afternoon | | ... |
| | Good evening | | ... |
| | ... | | ... |
| ... | ... | ... | ... |
| Person | Father | Pappy | ... |
| | Dad | | ... |
| | Papa | | ... |
| | ... | | ... |
| | Mother | Mammy | ... |
| | Mom | | ... |
| | mama | | ... |
| | ... | | ... |
| ... | ... | ... | ... |

FIG.4 ing Japanese Patent Application No. 2003-293567 filed in the Japanese Patent Office on Aug. 14, 2003, the entirety of which is incorporated by reference herein.

INFORMATION PROCESSING TERMINAL AND COMMUNICATION SYSTEM

TECHNICAL FIELD

The present invention relates to an information processing terminal that detects bio-information on a user thereof to make information communications reflecting the detected bio-information, and to a communications system including the information processing terminal.

This application claims the priority of the Japanese Patent Application No. 2003-293567 filed in the Japanese Patent Office on Aug. 14, 2003, the entirety of which is incorporated by reference herein.

BACKGROUND ART

The information processing terminal such as mobile phone, personal digital assistant (PDA) or the like can be connected to a network for sending and receiving an electronic mail (e-mail), and also to the so-called Internet. Also, the mobile phone and PDA have become amazingly prevalent, and there has become more popular the sending and reception of an e-mail by direct communications between the information processing terminals than that by the conventional communications, namely, indirect communications, between stationary personal computers (PC) via the Internet.

Along with the diversification of the electronic mail, various manners of e-mail sending and reception have been proposed. Normally, an e-mail is sent or received simply by clicking the 'Send and Receive' button. As one of such various e-mail sending and receiving manners, there is already available, for example, software which is to be used in the apparatus to display a virtual world in which a character such as a fictional pet or the like appearing on the screen of the apparatus carries a mail from or to the user in order to alarm the user of the e-mail sending or reception. This software provides such a function that the user can communicate with the pet or can occasionally receive a message from the pet.

Also, other manners of e-mail sending and reception are available. For example, simple "pictures" are provided which can be depicted with combinations of symbols to make text data that reflects user's emotion as much as possible. Further, pictographic characters are provided which are represented by special codes which are effective only between apparatuses suitable for exclusive use. Since these manners of e-mail sending and reception need not any dedicated software, they are simplest to use and are widely accepted.

Although an e-mail can be accompanied by video data and audio data, it is basically expressed with text data and thus is limited in incorporating "mood" and "user's sentiment" in a sentence.

On the other hand, there have been proposed techniques to control an apparatus in response to an internal state, such as emotion, of the apparatus user or the like. The conventional techniques are different from the e-mail sending and receiving method. For example, the Japanese Patent Application Laid Open No. 2001-34410 (Patent Document No. 1) has proposed a technique for safe handling of an apparatus, with which a sensor provided at an interface of the apparatus, such as a so-called mouse of a PC, joystick of an airplane or control stick of a crane vehicle, through which the user (pilot or operator) makes input of an intended operation to the apparatus, is used to detect a phenomenon of the user or operator, such as "unconscious straining", "cliff-hanging" or the like and estimate the emotion or sensitiveness of the user, pilot or operator, such as upsurge of sentiment, on the basis of the detected phenomenon for the purpose of safe handling of the apparatus.

Taking the electronic mail (e-mail) as an example, however, communication with a software-controlled character or mail from the character will not be in dialogue form in many cases because the response from the character is just a selected one of, for example, formulaic expressions or keywords prepared in advance. Also, a response can only be made in a predetermined pattern, and hence the e-mail is still limited in making an expression corresponding to "mood" or "user's sentiment".

Also, with the technique disclosed in the above Patent Document No. 1, the emotion or sensitiveness of the operator is detected. However, the detected operator's emotion or sensitiveness is fed back to the control of the apparatus being operated by the user, but not used as any communication tool responsive to the operator's emotion or sensitiveness.

DISCLOSURE OF THE INVENTION

It is therefore desirable to overcome the above-mentioned drawbacks of the conventional art by providing an improved and novel information processing terminal and a communications system using the information processing terminal.

It is also desirable to provide an information processing terminal that determines the psychology of the user on the basis of the bio-information on him or her and automatically generates information corresponding to the psychology.

It is also desirable to provide a communications system usable more widely as a communication tool to the advantage of the user by improving the entertaining property of an information processing terminal through automatic generation of information corresponding to the psychology of the user.

According to the present invention, there is provided an information processing terminal, wherein bio-information on the user is detected by a bio-information detecting means, psychology corresponding to the detected bio-information is analyzed based on the detected bio-information and the psychology corresponding to the detected bio-information, information matching the result of psychology analysis is generated by an information generating means, and the information is provided as an output by an output means.

The bio-information is at least one or a combination of selected ones, selected from among sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and $SPO_2$ (saturation of oxygen in the blood).

The information processing terminal includes a raw data storing means having raw data stored therein, and the information generating means may be adapted to generate information corresponding to the user's psychology from raw data selectively read out of the raw data storing means. Alternatively, the raw data storing means may be included in an external storage. In this case, the information generating means may be adapted to generate information matching the result of psychology analysis from raw data received from the external device. Especially, the information generated by the information generating means is a word or sentence including character data.

Also, the information processing terminal includes a word extracting means for extracting characteristic ones of words used in a sentence created by the user and a word storing means for storing the extracted words. In this case, the information generating means may be adapted to generate a sentence from the extracted words.

The output means for outputting the information may be either a displaying means for displaying a word or sentence generated by the information generating means or an audio output means for converting the word or sentence generated by the information generating means into an audio output.

According to the present invention, there is also provided a communications system including an information providing device and information processing terminals, wherein the information processing terminal detects bio-information on the user, analyzes the psychology of the user on the basis of the detected bio-information and sends the result of psychology analysis to the information providing device. The information providing device generates information matching the received result of psychology analysis from the raw data selectively read out of the raw data storing means and sends the information matching the received result of psychology analysis to the information processing terminal.

The information providing device includes a raw data storing means having raw data stored therein, and the information generating means may be adapted to generate information corresponding to the user's psychology from raw data selectively read out of the raw data storing means. Especially, the information generated by the information generating means is a word or sentence including character data and it is sent as an e-mail to the information processing terminal.

The information providing device further includes an audio output means for converting a word or sentence generated by the information generating means into an audio output and sending the audio output from the audio output means to the information processing terminal.

The bio-information may be at least one or a combination of selected ones, selected from among sweating, heartbeat, aspiration, blinking, eye movement, gaze time, pupil diameter, blood pressure, brain wave, body movement, body posture, skin temperature, skin electric resistance, MV (microvibration), myogenic potential and $SPO_2$ (saturation of oxygen in the blood).

According to the present invention, there is also provided a communications system including an information providing device and information processing terminal, wherein the information processing terminal detects bio-information on the user by means of a bio-information detecting means and sends it to the information providing device and the information providing device includes a raw data storing means having raw data stored therein and generates information corresponding to the received bio-information from raw data selectively read out of the raw data storing means. It should be noted here that the information generated by the information generating means is a word or sentence.

The information providing device according to the present invention may include a word extracting means for extracting characteristic ones of words used in a sentence created by the user and a word storing means for storing the extracted words. In this case, the information generating means may be adapted to generate a sentence from the extracted words.

The information output means may be either a displaying means for displaying a word or sentence generated by the information generating means or an audio output means for converting the word or sentence generated by the information generating means into an audio output.

Also, the bio-information may be at least one or a combination of selected ones, selected from among sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and $SPO_2$ (saturation of oxygen in the blood).

According to the present invention, there is also provided a communications system capable of information communications between communication devices via an information providing device, wherein the first one of the communication devices detects bio-information on the user by means of a bio-information detecting means, analyzes psychology corresponding to the detected bio-information by means of a psychology analyzing means and sends the result of psychology analysis to the information providing device by means of a transmitting means, and the information providing device generates information matching the received result of psychology analysis by means of an information generating means and sends the information matching the result of psychology analysis to the second communications device.

The information providing device includes a raw data storing means having raw data stored therein, and the information generating means may be adapted to generate information corresponding to the user's psychology from raw data selectively read out of the raw data storing means. Especially, the information generated by the information generating means is a word or sentence including character data.

Also, the information providing device includes a word extracting means for extracting characteristic ones of words used in a sentence created by the user and a word storing means for storing the extracted words. In this case, the information generating means may be adapted to generate a sentence from the extracted words.

The word or sentence generate as above may be sent as an e-mail by the transmitting means to the second communications device. Alternatively, the information providing device may include an audio converting means for converting a word or sentence generated by the information generating means into an audio output, and may send the audio output from the audio converting means to the second communications device. To send the audio output to the second communications device, the second communications device includes an audio output means that outputs the audio output converted by the audio converting means.

The bio-information may be at least one or a combination of selected ones, selected from among sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and $SPO_2$ (saturation of oxygen in the blood).

According to the present invention, there is also provided a communications system capable of information communications between communication devices via an information providing device, wherein the first one of the communication devices detects bio-information on the user by means of a bio-information detecting means and sends the detected bio-information to the information providing device by means of a transmitting means, and the information providing device analyzes psychology corresponding to the received bio-information by means of a psychology analyzing means, generates information matching the received result of psychology analysis by means of an information generating means and sends the information matching the result of psychology analysis to the second communications device.

The information providing device used in the communications system includes a raw data storing means having raw data stored therein, and the information generating means may be adapted to generate information corresponding to the user's psychology from raw data selectively read out of the raw data storing means. Especially, the information generated by the information generating means is a word or sentence including character data.

Also, the information providing device includes a word extracting means for extracting characteristic ones of words used in a sentence created by the user and a word storing means for storing the extracted words. In this case, the information generating means may be adapted to generate a sentence from the extracted words.

The word or sentence generate as above may be sent as an e-mail by the transmitting means to the second communications device. Alternatively, the information providing device may include an audio converting means for converting a word or sentence generated by the information generating means into an audio output, and may send the audio output from the audio converting means to the second communications device. To send the audio output to the second communications device, the second communications device includes an audio output means that outputs the audio output converted by the audio converting means.

The bio-information may be at least one or a combination of selected ones, selected from among sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and $SPO_2$ (saturation of oxygen in the blood).

In the information processing terminal according to the present invention, bio-information on the user is detected by the bio-information detecting means, psychology corresponding to the detected bio-information is analyzed based on the detecting bio-information and psychology corresponding to the detected bio-information, information matching the result of psychology analysis is generated by the information generating means, and the information matching the result of psychology analysis is displayed by the displaying means, whereby information corresponding to occasional psychology of the user, determined based on the bio-information on the user, can timely be displayed. Because the information processing terminal has a high entertaining property, the user will empathize with the displayed information and thus his or her psychology can be stabilized or improved.

In the communications system according to the present invention, bio-information on the user is detected, psychology corresponding to the detected bio-information is analyzed and the result of psychology analysis is sent to the information providing device. In the information providing device, information matching the received result of psychology analysis is generated from raw data selectively read out of the raw data storing means, and the information matching the result of psychology analysis is sent to the information processing terminal, whereby information corresponding to the psychology of the user, determined based on the bio-information on the user, can be provided. Especially, the information generated by the information generating means is a sentence. This sentence is sent as an e-mail. Thus, a sentence whose content will encourage or comfort the user or with which the user empathizes is sent as an e-mail, whereby the entertaining property of the information processing terminal can be improved.

Also, the communications system adapted according to the present invention to send information corresponding to the psychology of the user to a device designed by the information processing terminal can transmit "mood" and "user's sentiment" in a user-friendly form, which has been difficult to do by the conventional e-mail exchange and thus the communications system can effectively be used as a communication tool to the advantage of the user.

These objects and other objects, features and advantages of the present invention will become more apparent from the following detailed description of the best mode for carrying out the present invention when taken in conjunction with the accompanying drawings.

BRIEF DESCRIPTION OF THE DRAWINGS

FIG. 4 explains a raw word memory in which basic words and characteristic words are stored.

BEST MODE FOR CARRYING OUT THE INVENTION

Figure 1:
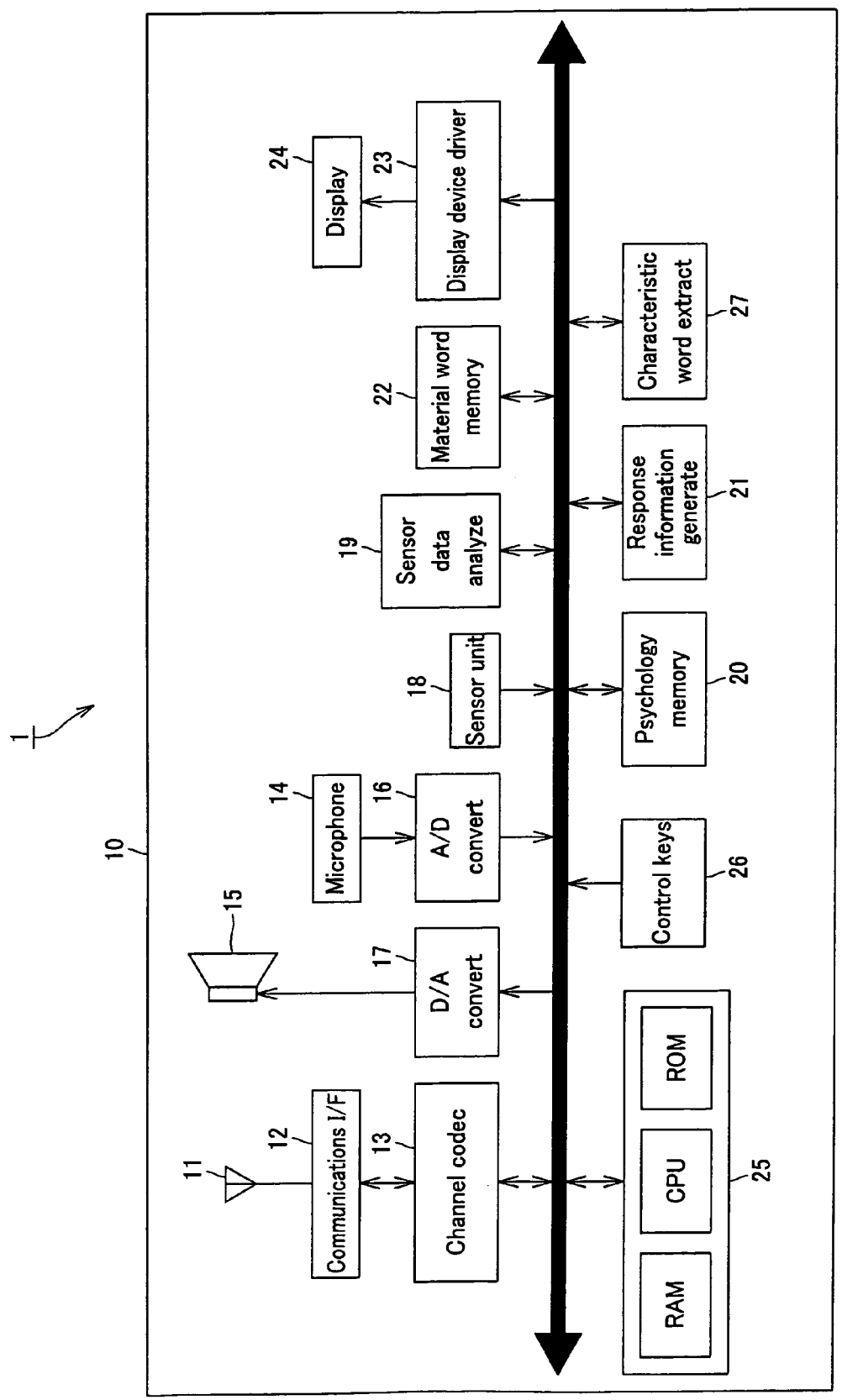
FIG. 1 is a schematic block diagram of a mobile phone according to the present invention.

The information processing terminal according to the present invention is, for example, a mobile phone or personal digital assistant. Including a bio-information detector to detect bio-information on the user of the information processing terminal, and a psychology analyzer to analyze psychology from the detected bio-information, the information processing terminal generates information matching the result of psychology analysis. More specifically, in case the information processing terminal is a mobile phone, a contact-type bio-sensor is provided at a portion the user touches most frequently, for example, on the back of a liquid crystal display casing or on control keys to detect bio-information data on the user.

The bio-information data includes sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and $SPO_2$ (saturation of oxygen in the blood) derived from biophenomena such as heart stroke, breathing, saturated blood oxygen level, eye movement, blood flow in the brain, blood function, physical exertion, etc., which can be measured by various measuring instruments such as an electrocardiograph, electromyograph, cranial voltmeter, infrared image intensity analyzer, pressure sensor, thermosensor, sudorometer, etc.

The data detected by such sensors are analyzed based on a bio-information data vs. psychology table prepared in advance. For example, in case it is analyzed that the user feels blue, the mobile phone will generate and display such audio data, video data or text data as will give the user a lift.

Information to vary or keep in phase with the user's psychology can be presented by various methods. Two typical methods to present text data will be explained below by way of example. The first one of the text data presentation methods is to display a sentence generated correspondingly to psychology as if it were a message sent to the user via e-mail, for example. Currently, there are prevailing mobile phones connectable to a network and capable of sending and receiving an e-mail. So, display of information matching the user's psychology generated by the mobile phone in the form of an e-mail will be friendly and familiar to the user. Further, storage of a characteristic word normally used by the user in creating a sentence as a material and usage of the characteristic word in creating text data corresponding to the user's psychology will be more familiar to the user.

The second one of the text data presentation methods is to send bio-information on the user to a management device or the like and actually receive an e-mail corresponding to psychology from the management device via a network. This method is advantageous in that the mobile phone has only to be designed for detection of at bio-information data and information for appropriate transmission of psychology of the user can be sent to others.

In case response information to be presented is audio data, a word or sentence created correspondingly to user's psychology analyzed from detected bio-information is provided as a speech in a predetermined timing. Also for outputting a speech, the mobile phone may be designed to output a word or sentence as a speech through text-speech synthesis or the text-speech synthesis may be done by a management device or the like in a network.

By analyzing psychology from detected bio-information and presenting information matching the result of psychology analysis or sending the information matching the user's psychology to others as above, the object of improving the entertaining property of a mobile phone and using the mobile phone as a communications tool widely to the advantage of the user has been attained.

The mobile phone according to the present invention will be described in detail below with reference to the accompanying drawings.

Referring now to FIG. 1, there is schematically illustrated in the form of a block diagram the mobile phone according to the present invention. The mobile phone is generally indicated with a reference numeral 1. As shown, having a body 10 including an antenna 11, communications interface (I/F) 12 and transmission channel codec 13, the mobile phone 1 is designed to send and receive data etc. between itself and a base station (not shown). Also, it includes a microphone 14 to convert received an audio signal into a digital signal, speaker 15 to output a speech, A-D conversion circuit 16 to convert a received audio signal into a digital signal and a D-A conversion circuit 17 to convert a digital signal into an analog signal. In addition, the mobile phone 1 has the basic structure (not shown) of mobile phones.

Also, the mobile phone 1 includes sensors 18 to detect bio-information on the user. Being carried in a packet or held in hand, the mobile phone 1 is kept in contact with part of the user's body for a relatively long time. So, the sensors 18 should preferably be of a type capable of detecting bio-information data that can be detected while being in contact with the user's body. In this embodiment, the sensors 18 include a skin electric resistance sensor, sweating sensor and skin surface temperature sensor, and these sensors are provided on part of the housing surface of the mobile phone body, for example, on the rear of the phone body or control button. In addition, there can be utilized the characteristics of bio-information that the heart rate is stable when the user is relaxed, while it is higher than the normal one when the user is astonished or excited. Examples of the bio-sensors that may be adopted in this embodiment will be described in detail later.

Bio-information data detected by the sensors 18 are sent to a sensor data analyzer 19 in which psychology of the user will be analyzed based on the correspondence between bio-information data stored in a psychology memory 20 and psychology. The bio-information data such as "skin electric resistance", "sweating rate" and "skin temperature", detected with one motion or sentiment of the user are similar to those detected with any other motion or sentiment as the case may be. However, each of such bio-information data delicately varies from an excited state in which the user is given a lift with good feeling to an excited state in which the user is irritated with discomfort. On this account, the sensor data analyzer 19 extracts a characteristic signal pattern from bio-information data detected by the sensors 18 and analyzes psychology corresponding to the extracted signal pattern. In this embodiment, the psychology includes, for example, "pleased and delightful", "discouraged", "excited", etc. and these states of mind are stored in association with bio-information data in the psychology memory 20. When the bio-information data are detected by the sensors 18, the sensor data analyzer 19 selectively reads psychology most matching the bio-information data out of the psychology memory 20.

Figure 2:
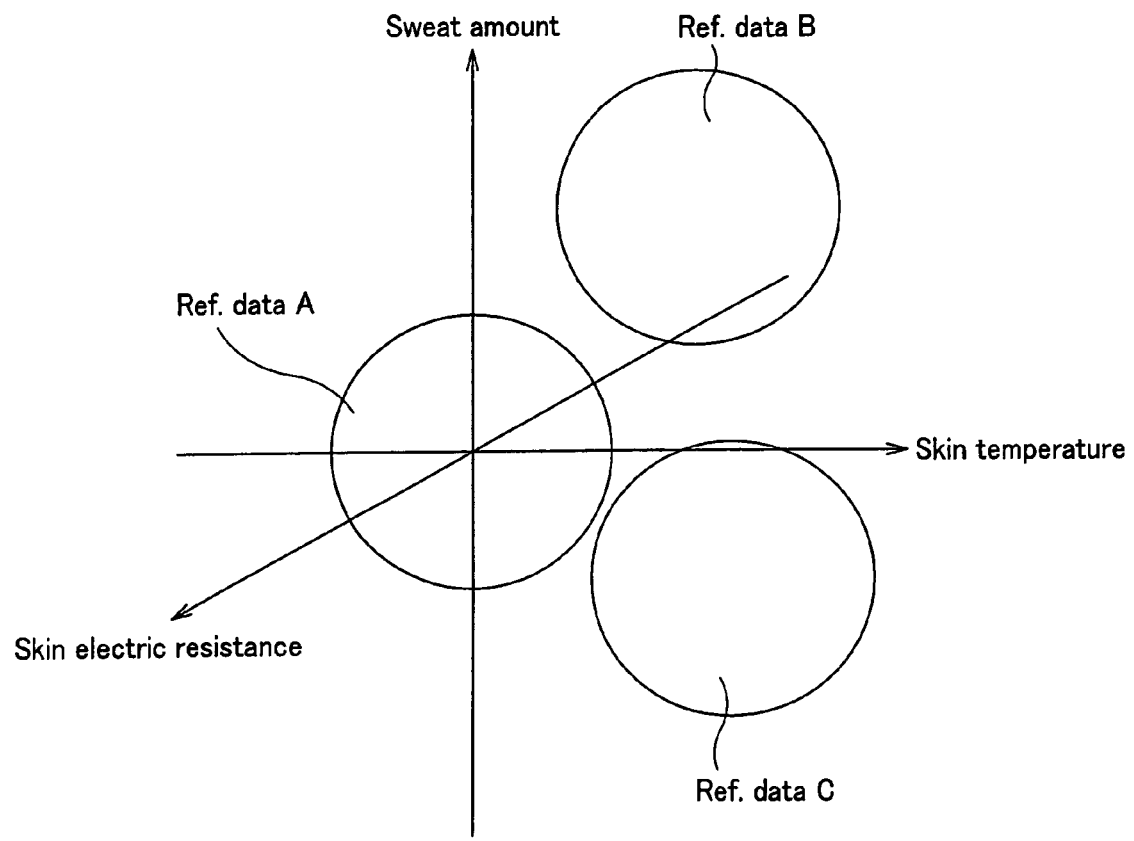
FIG. 2 shows a distribution of reference data in a three-dimensional spatial coordinate system.

For analysis by the sensor data analyzer 19, reference data on the user are pre-defined by pre-storing a range of sensor data indicative of temper or depression in the memory, with a controller 25 explicitly directing the user to acquire bio-information data in the normal condition, or through automatic detection of bio-information data at regular intervals, determination of a distribution of the detected data and statistic detection of each psychology. In case three bio-information data "skin electric resistance", "sweating rate" and "skin temperature" are used as in this embodiment, these sensor data may be allocated to a three-dimensional spatial coordinate system as shown in FIG. 2 to sort the reference data as "spatial domain" for sorting psychology. It should be noted that in FIG. 2, reference data A indicates a normal state and reference data B indicate an excited state.

The bio-information data may be ones from which the sentiment, psychology, physical condition, etc. of the user can quantitatively be evaluated and they are not limited to those referred to herein by way of example. The psychology can be analyzed using the aforementioned correspondence table. Alternatively, it can be analyzed using an algorithm or the like, if any, by which psychology can be calculated directly from bio-information data.

The mobile phone 1 also includes a response information generator 21 that generates a text as response information matching the result of psychology analysis. The response information generator 21 generates, correspondingly to the result of psychology analysis, for example, a response word or sentence from a word whose meaning is "to encourage or comfort" when the user is depressed or from a word whose meaning is "to appease" when the user is excited, and displays such a response information as if the mobile phone 1 had sent it to the user. The words used in the text generation are sorted like "encourage or comfort" and "appease" and pre-stored in a material word memory 22.

The mobile phone 1 according to the present invention is used with software that enables a character such as a virtual pet appearing on the screen of the mobile phone to carry a mail or receive a mail addressed to the user from a communication-destination character in a virtual world. More specifically, the mobile phone 1 generates a sentence on the basis of the user's psychology analyzed from bio-information data and with reference to the material word memory 22 and displays the process of the sentence generation as if the above character carried the sentence as a mail. For example, when the result of psychology analysis is such that the user is depressed, the character will carry a mail that encourages or comforts the user. When the psychology analysis result is such that the user feels happy, the character will carry a mail reading that the character also feels happy with the user. The text thus generated is displayed on a display unit 24 by a display device driver 23. The display unit 24 uses an LCD (liquid crystal display).

The mobile phone 1 according to the present invention is totally controlled by a controller 25 including a CPU, ROM having stored therein programs for running the CPU and information on various settings, and a RAM as a work area of the CPU. It accepts a user's instruction and choice from control keys 26 as necessary. An operation is performed based on an instruction or choice from the control keys 26 as the case may be. More specifically, the controller 25 implements, according to programs stored in the ROM, generation of response information matching the result of psychology analysis of user's bio-information data, extraction of a characteristic word from a sentence created by the user, which will be described in detail later, and the like. Each of memories provided in the body 10 are semiconductor memories but it may be of any type if it would retain data. Also, each of the memories may be a logical area physically separated from one recording medium.

Figure 3:
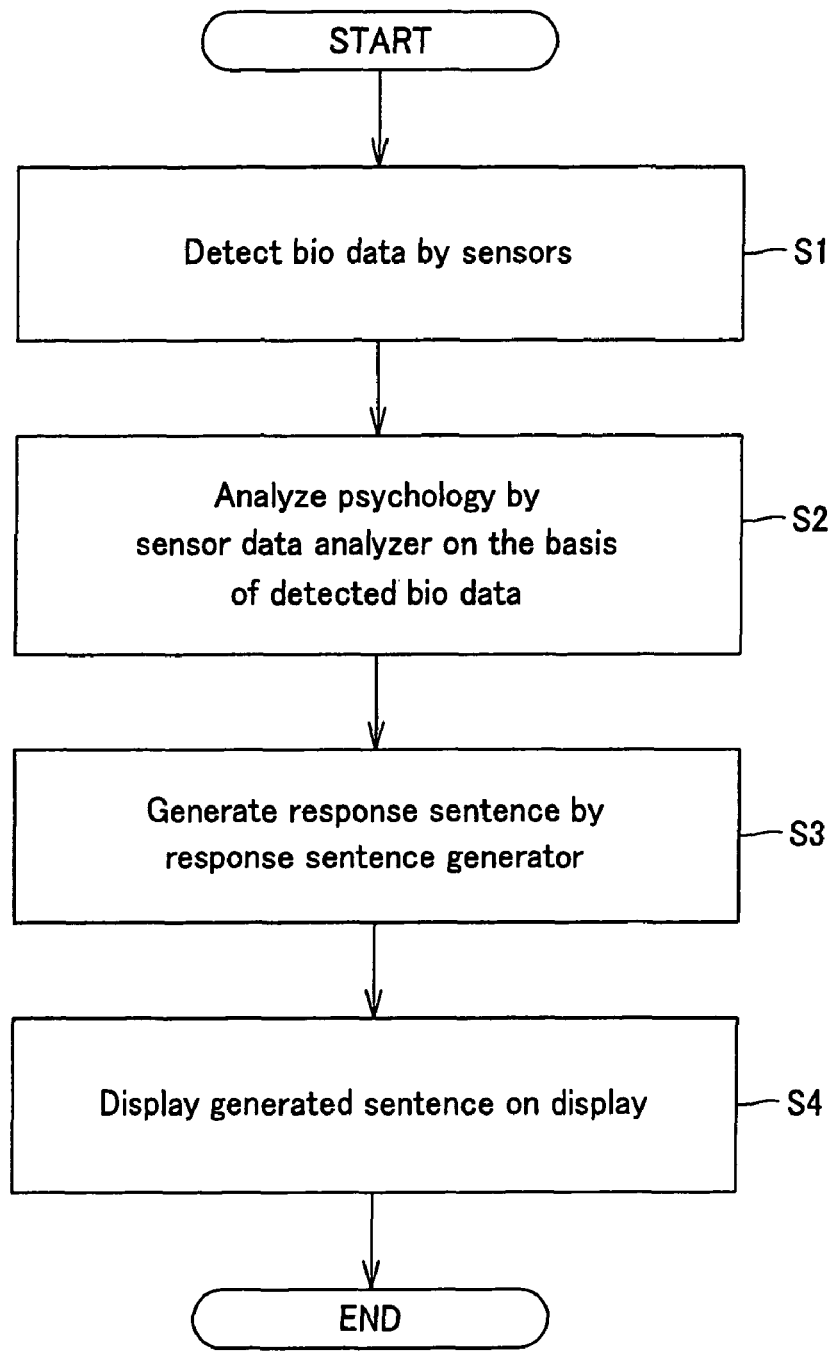
FIG. 3 shows a flow of operations made by the mobile phone in generating a response sentence on the basis of user's psychology analyzed based on detected bio-information data.

Next, the procedure for generating a response sentence through analysis of the user's psychology from detected bio-information data will be described with reference to FIG. 3.

In the mobile phone 1, bio-information data are detected in step S1, and the detected bio-information data are collated with the psychology sorted by way of example as in FIG. 2 to determine the user's psychology. In step S2, the psychology thus determined is sent to the response information generator 21. In step S3, the response information generator 21 selectively reads words corresponding to the detected psychology out of the material word memory 22 and generates a response sentence. It should be noted here that words to be used in generation of a sentence are sorted like "encourage or comfort" and "appease" and stored in the material word memory 22. For example, when the user feels depressed, a word sorted as "encourage or comfort" is used to generate a response sentence. When the user is excited, a word sorted as "appease" is used to generate a response sentence. In step S4, a sentence generated by the response information generator 21 is displayed on the LCD display.

In this embodiment, the mobile phone 1 includes a characteristic word extraction unit 27 that extracts characteristic words frequently used by the user and stores them in association with basic words pre-stored in the material word memory 22. That is, the characteristic word extraction unit 27 automatically registers such characteristic words into a so-called user-dedicated dictionary. Here will be explained examples of words stored in the material word memory 22 with reference to FIG. 4. The material word memory 22 has basic words stored therein being sorted according to categories such as personal words, salutation, etc. and has extracted characteristic words stored in association with the categories.

In case the user has an inclination to frequently use "Good day" as a salutation through the morning, afternoon and night in his mail sentence and to write part of a representation in kana, for example, the mobile phone 1 extracts such characteristic words and stores them in the material word memory 22. Using the characteristic words stored in the material word memory 22, the response sentence generator 21 can generate sentences such as "Good day! You look not fine. What's the matter?", for example. Combining already prepared sentence examples and basic words and converting the combination into words the user frequently uses when generating a response sentence by means of the material word member 22, the response information generator 21 can generate a response sentence that will have the user feel an increased affinity to the mobile phone 1 and a fictional character appearing on the screen of the mobile phone 1.

The mobile phone 1 has the entertaining property thereof improved by providing, depending upon the psychology of the user, an illusion that the mobile phone itself talks to the user or a message has come from a fictional pet. For example, when the user has become excited due to a battle of words with his or her party, a sentence to "appease" the user will be displayed correspondingly to his psychology when he is through the talking over the phone. Also, when the user has become depressed due to a battle of words with his party, a sentence to "comfort" him will be displayed correspondingly to his psychology when he is through the talking.

Therefore, the mobile phone 1 according to the present invention can be used by the user with an increased affinity thereto and work more than a simple communications tool.

Figure 5:
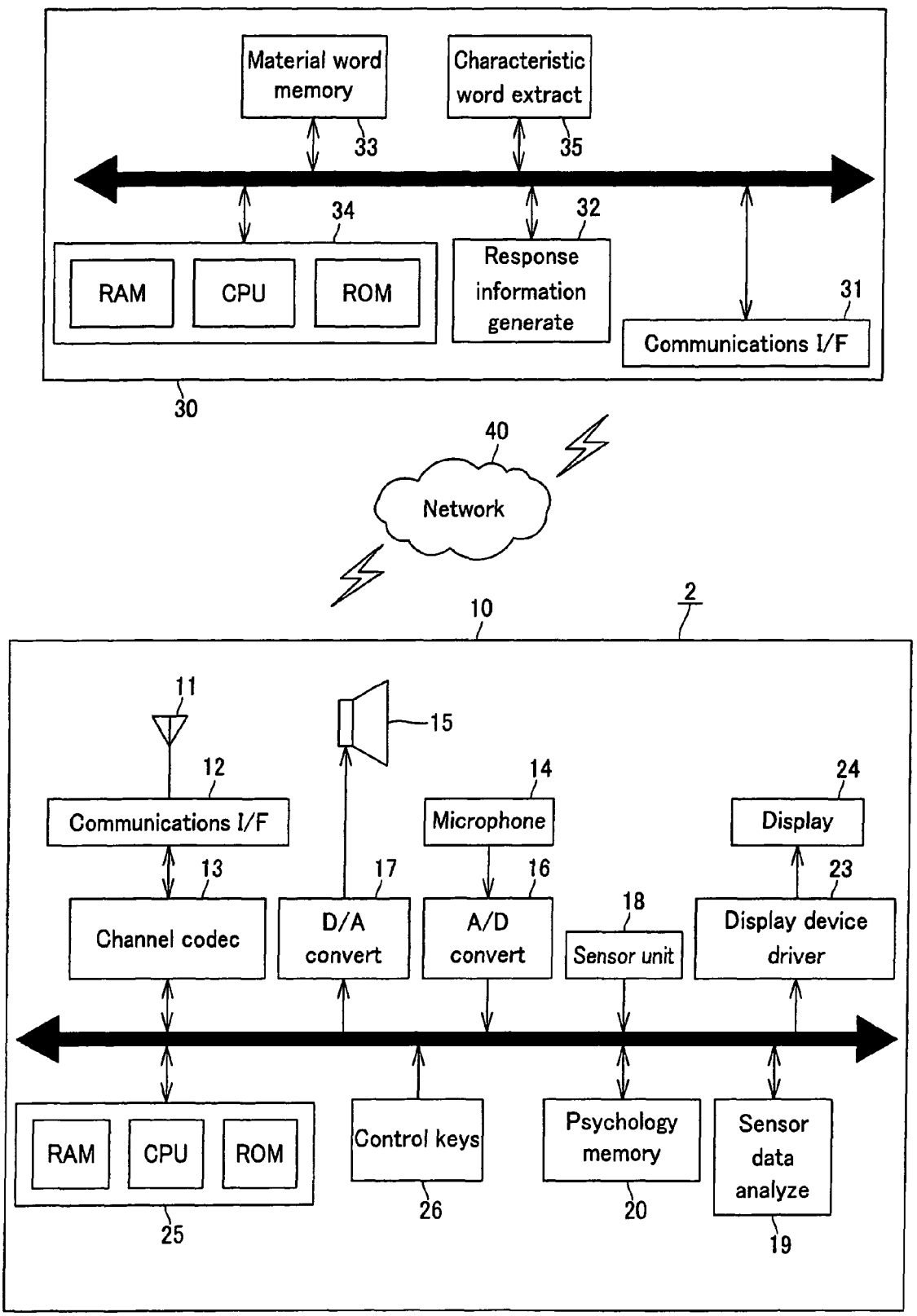
FIG. 5 is a schematic block diagram of the communications system according to the present invention.

Next, the present invention will be described in detail below concerning the communications system as another embodiment thereof, including a material word memory and response information generator in a server provided in a network, with reference to FIG. 5. Because of this communications system, the portable phone can be constructed more simply. It should be noted that the same components as those in FIG. 1 are indicated with the same reference numerals as used in FIG. 1 and will not be described in detail being regarded as having the same functions as the components shown in FIG. 1.

The communications system includes a mobile phone 2 comprises of an antenna 11, communications interface (I/F) 12, channel codec 13, microphone 14 to receive user's voice, speaker 15 to output a speech, A-D converter 16 to convert a received audio signal into a digital signal, D-A converter 17 to convert the digital signal into an analog signal, sensors 18 to detect bio-information data on the user, sensor data analyzer 19 to extract characteristic signal pattern from the bio-information data detected by the sensors 18 and analyze psychology corresponding to the extracted signal pattern, psychology memory 20 which is referred to by the sensor data analyzer 19, controller 25 to control all the above components, control keys 26 to accept user's operations, display device driver 23 and a display 24.

Also, the communications system includes a server 30 comprised of a communications interface 31 to receive psychology sent from the mobile phone 2 and response information to be displayed on the mobile phone 2, response information generator 32 to generate response information correspondingly to the psychology sent from the mobile phone 2, material word memory 33 which is referred to by the response information generator 32 and a controller 34 to control all the above components to control the sequence of operations of generating response information matching the psychology sent from the mobile phone 2 and sending the response information to the mobile phone 2. The communications system is radio- or cable-connected to the mobile phone 2 and a network 40.

In the communications system, for example, when the user is through talking on the mobile phone 2, the analyzed psychology is sent to the server 30, response information matching the psychology is generated in the server 30 and returned to the mobile phone 2. Similarly to the mobile phone itself, the communications system can provide, depending upon the psychology of the user, an illusion that the mobile phone itself talks to the user or a message has come from a fictional pet. Thus it can improve the entertaining property of the mobile phone and permits the mobile phone to be constructed more simply.

Note that for more development of the communications system in which the server in the network has the function of generating response information, the sensor data analyzer 19 and the psychology memory 20 which is referred to during psychology analysis may be provided in the server. Also, a characteristic word extraction unit 35 may be provided in the server. Thus, the mobile phone 2 can be constructed more simply and the capacity of the psychology memory is not limited so that information on psychology corresponding to more bio-information data can be stored in the memory.

Also note that although the response information generated in accordance with the psychology of the user is a sentence in each of the above embodiments and variants, it may be a word or a sequence of words or a so-called pictogram. Also, the mobile phone 2 may be adapted to make text-speech synthesis of such word or words or sentence and output the word or sentence as a speech. Further, the response information may be an animation in which the facial expression or behavior of a character is altered depending upon the psychology of the user, image data such a landscape or the like as will relax the user or such audio data including melody and music as will make the user feel tempered or high. Of course, response information may be generated by combining these information together.

In the latter case, the speech-output data corresponding to pictogram, word and sentence, material images for animation, image data such as a landscape, audio data, etc., are prepared in a memory corresponding to the material word memory 22 having stored therein data for generation of sentences, and extracted by the response information generator 21 from the memory to generate response information.

Figure 6:
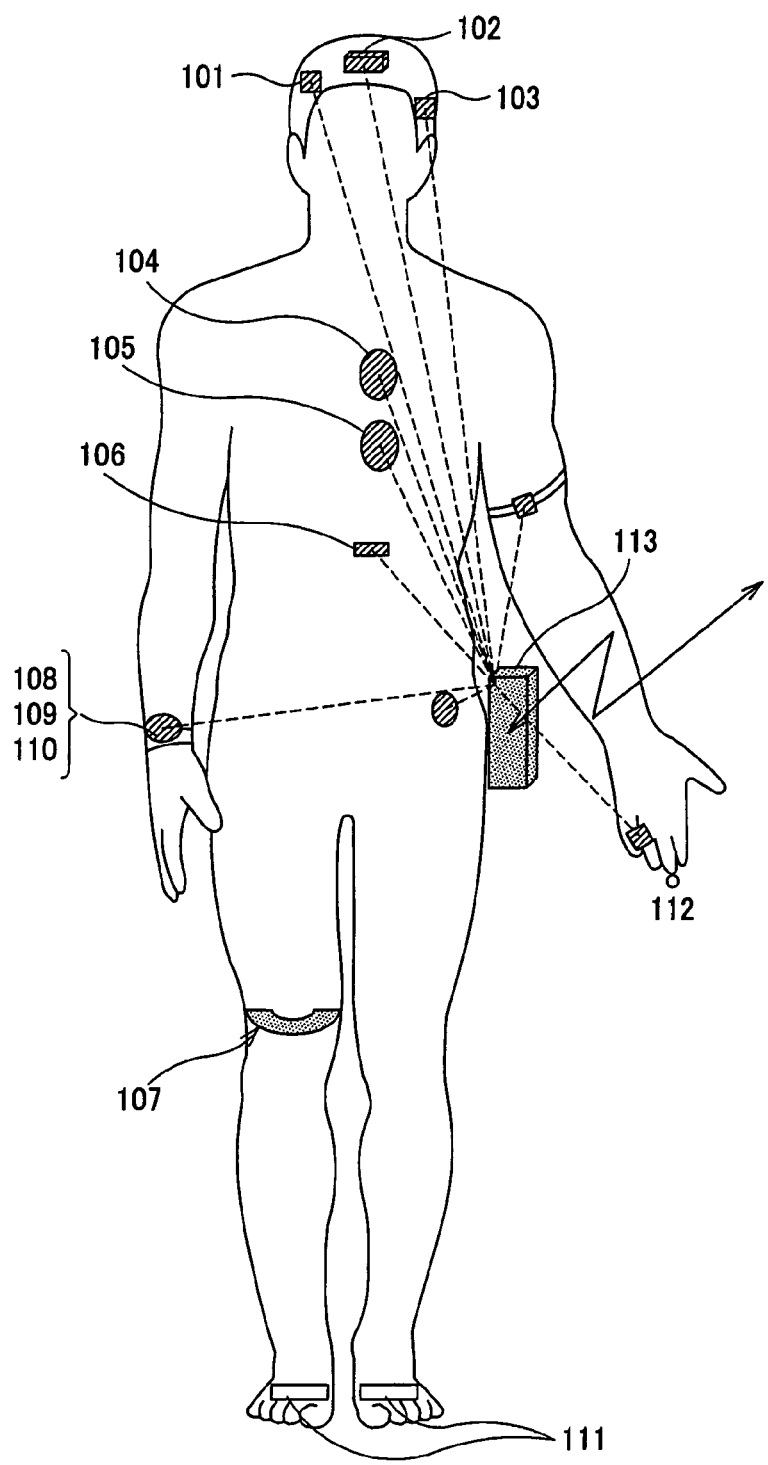
FIG. 6 schematically illustrates another example of bio-sensor usable in the present invention.

Here will be explained a bio-sensor usable in the present invention. The sensor may not be integral with the body of the mobile phone as in the foregoing description of the embodiment of the present invention. For example, the bio-sensor may be provided separately from the body 10 and adapted to send detected data to the mobile phone 1, whereby it is possible to acquire not only bio data detected with the sensor put in contact with the user's body but also more bio data. That is, there may be used sensors capable of detecting sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and $SPO_2$ (saturation of oxygen in the blood) derived from biophenomena such as heart stroke, breathing, saturated blood oxygen level, eye movement, blood flow in the brain, blood function, physical exertion, etc. Other examples of the bio-sensor usable in the present invention will be described below with reference to FIG. 6.

The sensors 18 include, for example, a rheometer 101, electroencephalograph 102, eye movement sensor 103, electrocardiograph 104, oscillation gyroscope 105, acceleration sensor 106, muscle sound measuring instrument 107, skin temperature sensor 108, body movement acceleration sensor 109, skin conductivity sensor 110, foot pressure sensor 111, pulse meter 112, etc. The rheometer 101 emits infrared rays to the user's body and detects reflected infrared rays to measure the blood flow in the brain and blood oxygen level. The electroencephalograph 102 measures the brain waves such as α-wave, β-wave, etc. on the basis of a current flowing through the brain. The eye movement sensor 103 is mounted on the user's head to measure the frequency of an eyeball movement on the basis of a potential in the head. Alternatively, a camcorder may be used to detect the eyeball movement. The electrocardiograph 104 measures the user's heart rate on the basis of a current generated by the cardiac muscle. The oscillation gyroscope 105 measures the breast motion and breathing rate on the basis of an angular velocity. The muscle sound measuring instrument 107 measures the micro vibration generated on the body surface at the time of muscle contraction to determine muscle sound that is considered to have a relation with fatigue. The skin temperature sensor 108 measures the bodily temperature. The skin conductivity sensor 110 measures the sweating rate on the basis of the skin electric resistance. The foot pressure sensor 111 detects the moving distance and motion of the user. Some of the above bio-sensors are designed as lightweight like a wrist band, circlet or the like as to be wearable on the user's body. A sensor installable on a control part of the mobile phone can detect bio-information data when the user touches the control part to operate the mobile phone. Also, it is also possible to analyze bio-information by analyzing characteristics of a user's voice print from audio data supplied to the mobile phone.

Since more complex bio-information data can be detected using the above-mentioned sensors, psychology can be analyzed with an improved accuracy and a wider variety of psychology can be analyzed.

In the foregoing, the present invention has been described in detail concerning certain preferred embodiments thereof as examples with reference to the accompanying drawings. However, it should be understood by those ordinarily skilled in the art that the present invention is not limited to the embodiments but can be modified in various manners, constructed alternatively or embodied in various other forms without departing from the scope and spirit thereof as set forth and defined in the appended claims.

INDUSTRIAL APPLICABILITY

As having been described in the foregoing, the present invention is applicable to the mobile phone, but it is also applicable to an electronic device which is always carried and used by the user to improve the entertaining property of the device. Therefore, the electronic device can be used by the user with an increased affinity thereto and work more than a simple communications tool.

The invention claimed is:

1. An information processing terminal, comprising:
bio-information detecting means for detecting bio-information on a user;
psychology analyzing means for analyzing the user's psychology based on the detected bio-information;
word extracting means for extracting characteristic ones of words used in a sentence created by the user;
word storing means for storing the extracted words;
information generating means for generating information matching a result of the psychology analysis including a word or a sentence generated from the extracted words; and
output means for providing the generated information as an output.

2. The information processing terminal according to claim 1, wherein the bio-information is at least one or a combination of selected ones, selected from among sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and SPO2 (saturation of oxygen in the blood).

3. The information processing terminal according to claim 1, further comprising raw data storing means having raw data stored therein, the information generating means being adapted to generate information corresponding to the user's psychology from raw data selectively read out of the raw data storing means.

4. The information processing terminal according to claim 1, further comprising transmitting/receiving means for sending the result of psychology analysis to an external device and receiving raw data selected by the external device on the basis of the received result of psychology analysis,
the information generating means being adapted to generate information matching the result of psychology analysis from the raw data received from the external device.

5. The information processing terminal according to claim 1, wherein the output means is displaying means for displaying a word or sentence generated by the information generating means.

6. The information processing terminal according to claim 1, wherein the output means includes audio output means for converting the word or sentence generated by the information generating means into an audio output.

7. A communications system including an information providing device and information processing terminals, an information processing terminal comprising:
bio-information detecting means for detecting bio-information on a user,
psychology analyzing means for analyzing the user's psychology based on the detected bio-information,
word extracting means for extracting characteristic ones of words used in a sentence created by the user,
word storing means for storing the extracted words,
transmitting/receiving means for sending a result of the psychology analysis to the information providing device and receiving information generated by the information providing device on the basis of the result of psychology analysis and matching the result of psychology analysis, the information including a word or a sentence generated from the extracted words, and
output means for providing the received information as an output.

8. The communications system according to claim 7, wherein the information providing device includes a raw data storing means having raw data stored therein,
the information generating means being adapted to generate information corresponding to the user's psychology from raw data selectively read out of the raw data storing means.

9. The communications system according to claim 7, wherein the transmitting means in the information providing device sends the word or sentence as an e-mail to the information processing terminal.

10. The communications system according to claim 7, wherein the information providing device further includes audio output means for converting a word or sentence generated by the information generating means into an audio output,
the audio output from the audio output means being sent to the information processing terminal.

11. The communications system according to claim 7, wherein the information processing terminal further includes audio output means for converting a word or sentence received by the transmitting/receiving means into an audio output,
the audio output from the audio output means being provided from the output means.

12. The communications system according to claim 7, wherein the bio-information is at least one or a combination of selected ones, selected from among sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and SPO2 (saturation of oxygen in the blood).

13. A communications system including an information providing device and an information processing terminal, wherein:
the information processing terminal includes bio-information detecting means for detecting bio-information on a user, word extracting means for extracting characteristic ones of words used in a sentence created by the user, word storing means for storing the extracted words, transmitting/receiving means for sending the detected bio-information and the extracted words to the information providing device and receiving information generated by the information providing device on the basis of the bio-information, and output means for providing the received information as an output; and
the information providing device includes psychology analyzing means for analyzing the user's psychology based on the received bio-information, information generating means for generating information matching a result of the psychology analysis, the information including a word or a sentence generated from the extracted words, and transmitting means for sending the generated information to the information processing terminal.

14. The communications system according to claim 13, wherein the information providing device includes raw data storing means having raw data stored therein,
the information generating means being adapted to generate information corresponding to the user's psychology from raw data selectively read out of the raw data storing means.

15. The communications system according to claim 13, wherein the transmitting means in the information providing device sends the word or sentence as an e-mail to the information processing terminal.

16. The communications system according to claim 13, wherein the information providing device further includes audio output means for converting a word or sentence generated by the information generating means into an audio output,
the audio output from the audio output means being sent to the information processing terminal.

17. The communications system according to claim 13, wherein the information processing terminal further includes audio output means for converting a word or sentence received by the transmitting/receiving means into an audio output,
the audio output from the audio output means being provided from the output means.

18. The communications system according to claim 13, wherein the bio-information is at least one or a combination of selected ones, selected from among sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and SPO2 (saturation of oxygen in the blood).

19. A communications system capable of information communications between communication devices via an information providing device, the system comprising:
a first communications device including:
bio-information detecting means for detecting bio-information on the user;

psychology analyzing means for analyzing psychology based on the detected bio-information;

word extracting means for extracting characteristic ones of words used in a sentence created by the user;

word storing means for storing the extracted words; and transmitting means for sending a result of the psychology analysis and the extracted words to the information providing device;

information generating means for generating information matching the received result of the psychology analysis, the information including a word or a sentence generated from the extracted words; and transmitting means for sending information matching the result of the psychology analysis to a second communications device.

20. The communications system according to claim 19, wherein the information providing device includes raw data storing means having raw data stored therein, the information generating means being adapted to generate information corresponding to the user's psychology from raw data selectively read out of the raw data storing means.

21. The communications system according to claim 19, wherein the transmitting means in the information providing device sends the word or sentence as an e-mail.

22. The communications system according to claim 21, wherein the second communications device includes output means for providing the received word or sentence as an output, the output means being displaying means for displaying the received word or sentence.

23. The communications system according to claim 19, wherein the information providing device further includes audio output means for converting a word or sentence generated by the information generating means into an audio output, the audio output from the audio output means being sent to the second communications device.

24. The communications system according to claim 23, wherein the second communications device includes audio output means for providing a word or sentence received as an audio output to outside.

25. The communications system according to claim 19, wherein the bio-information is at least one or a combination of selected ones, selected from among sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and SPO2 (saturation of oxygen in the blood).

26. A communications system capable of information communications between communication devices via an information providing device, the system comprising:

a first communications device including:

bio-information detecting means for detecting bio-information on the user;

word extracting means for extracting characteristic ones of words used in a sentence created by the user;

word storing means for storing the extracted words; and transmitting means for sending the detected bio-information and the extracted words to the information providing device;

psychology analyzing means for analyzing psychology based on the received bio-information;

information generating means for generating information matching the received result of the psychology analysis, the information including a word or a sentence generated from the extracted words; and an information providing device including transmitting means for sending the information matching the result of the psychology analysis to a second communications device.

27. The communications system according to claim 26, wherein the information providing device includes raw data storing means having raw data stored therein, the information generating means being adapted to generate information matching the result of psychology analysis from raw data selectively read out of the raw data storing means.

28. The communications system according to claim 26, wherein the transmitting means in the information providing device sends the word or sentence as an e-mail.

29. The communications system according to claim 26, wherein the second communications device includes output means for providing the received word or sentence as an output, the output means being displaying means for displaying the received word or sentence.

30. The communications system according to claim 26, wherein the information providing device further includes audio output means for converting a word or sentence generated by the information generating means into an audio output, the audio output from the audio output means being sent to the information processing terminal.

31. The communications system according to claim 30, wherein the second communications device includes audio output means for providing a word or sentence received as an audio output to outside.

32. The communications system according to claim 26, wherein the bio-information is at least one or a combination of selected ones, selected from among sweating, heartbeat, pulse-beat, aspiration, blinking, eye movement, gaze time, pupil diameter, blood pressure, brain wave, body movement, body posture, skin temperature, skin electric resistance, MV (microvibration), myogenic potential and SPO2 (saturation of oxygen in the blood).

* * * * *